United States Patent [19]
Lin

[11] Patent Number: 5,905,162
[45] Date of Patent: May 18, 1999

[54] ENHANCED PRODUCTION OF BRIDGED HAFNOCENES

[75] Inventor: Ronny W. Lin, Baton Rouge, La.

[73] Assignee: Albemarle Corporation, Richmond, Va.

[21] Appl. No.: 09/057,178

[22] Filed: Apr. 8, 1998

Related U.S. Application Data

[63] Continuation-in-part of application No. 08/909,648, Aug. 12, 1997, abandoned.

[51] Int. Cl.$^6$ .............................. C07F 17/00; C07F 7/00
[52] U.S. Cl. .............................. 556/11; 556/12; 556/53; 526/160; 526/943; 502/103; 502/117
[58] Field of Search .............................. 556/11, 12, 53; 526/160, 943; 502/103, 117

[56] References Cited

U.S. PATENT DOCUMENTS

| | | | |
|---|---|---|---|
| 4,794,096 | 12/1988 | Ewen | 502/117 |
| 5,017,714 | 5/1991 | Welborn, Jr. | 556/12 |
| 5,036,034 | 7/1991 | Ewen | 502/117 |
| 5,036,035 | 7/1991 | Baba et al. | 502/221 |
| 5,145,819 | 9/1992 | Winter et al. | 502/117 |
| 5,264,590 | 11/1993 | Strickler | 549/208 |
| 5,296,434 | 3/1994 | Karl et al. | 502/117 |
| 5,302,733 | 4/1994 | Diefenbach et al. | 556/11 |
| 5,324,800 | 6/1994 | Welborn, Jr. et al. | 526/160 |
| 5,329,033 | 7/1994 | Spaleck et al. | 556/53 |
| 5,336,795 | 8/1994 | Lisowsky | 556/56 |
| 5,399,636 | 3/1995 | Alt et al. | 526/129 |
| 5,455,365 | 10/1995 | Winter et al. | 556/7 |
| 5,455,366 | 10/1995 | Rohrmann et al. | 556/8 |
| 5,532,396 | 7/1996 | Winter et al. | 556/11 |
| 5,556,997 | 9/1996 | Strickler et al. | 556/11 |
| 5,679,811 | 10/1997 | Winter et al. | 556/7 |
| 5,760,262 | 6/1998 | DeSoto et al. | 556/11 |
| 5,874,175 | 12/1998 | Strickler et al. | 556/11 |

FOREIGN PATENT DOCUMENTS 0709393  5/1996  European Pat. Off. .

OTHER PUBLICATIONS

Chemical Abstracts, vol. 121, No. 5, Aug. 1994, Takechi, Eiji et al., "Manufacture of Halogenated Metallocenes".
Chemical Abstracts, vol. 120 No. 13, Mar. 1994, Takechi, Eiji et al., "Preparation of Metallocene Halides".

*Primary Examiner*—Porfirio Nazario-Gonzalez
*Attorney, Agent, or Firm*—Philip M. Pippenger

[57] ABSTRACT

Racemic, bridged hafnocene is produced in enhanced yield by reacting a hafnium halide-aliphatic polyether adduct that has been formed and/or heated at one or more temperatures of at least about 40° C., and a metallated bis (cyclopentadienyl-moiety-containing) ligand, at one or more temperatures for a sufficient period of time such that a racemic, bridged hafnocene is produced. The reaction is performed in the substantial absence of tetrahydrofuran and/or any other ether solvent or diluent that causes the formation of a tarry residue in the reaction mixture.

21 Claims, No Drawings

ENHANCED PRODUCTION OF BRIDGED HAFNOCENES

REFERENCE TO RELATED APPLICATION

This is a continuation-in-part of commonly-owned prior application Ser. No. 08/909,648, filed Aug. 12, 1997, abandoned.

TECHNICAL FIELD

This invention relates to the production of hafnocenes by a highly efficacious process, which makes possible the formation of the desired racemic hafnocenes in higher yields and with better product quality at lower cost.

BACKGROUND

Chiral hafnocenes are useful for the synthesis of polyolefins. The racemic form of these hafnocenes provides stereoregular poly(alpha-olefins). In addition, the racemic form of these hafnocenes is considerably more catalytically active than the meso form, which produces only atactic polymers. Chiral hafnocenes and their use as catalysts in forming isotactic olefin polymers are described, for example, in U.S. Pat. Nos. 4,794,096; 5,017,714; 5,036,035; 5,036,034; 5,145,819; 5,296,434; 5,324,800; 5,329,033; 5,399,636; 5,455,365; 5,455,366; 5,532,396; and 5,556,997, the full disclosures of which are incorporated herein by reference.

It has been discovered that although hafnium is a member of Group 4, in the synthesis of metallocenes hafnium reactants can behave in a remarkably different manner from corresponding titanium or zirconium compounds. In particular, as shown by my colleagues, S. P. Diefenbach, M. S. Ao, J. M. Power and J. R. Strickler in U.S. Pat. No. 5,302,733, $ZrCl_4$ readily forms a tetrahydrofuran complex $ZrCl_4(THF)_2$ by addition of THF to slurry of $ZrCl_4$ in a medium such as methylene chloride or hexanes. Moreover the $ZrCl_4(THF)_2$ complex can be reacted in tetrahydrofuran with lithium derivatives of various silicon-containing cyclopentadienyl ligands such as the dilithio derivative of 1,1'-dimethylsilanylenebis(indene)ethyl etherate to produce racemic bridged zirconocenes such as rac-[1,1'-dimethylsilanylenebis(indenylzirconium dichloride. In fact this reaction was successfully performed at reaction temperatures between 50 and 54° C. (note Example 3 of U.S. Pat. No. 5,302,733). In sharp contrast, if the same reaction is attempted with $HfCl_4$, copious amounts of tar are produced and the yield of isolatable racemic isomer of the bridged hafnocene, so low as to be practically non-existent. Furthermore, the zirconocene is stable in THF solution whereas the hafnocene is very unstable in THF solvent even at room temperature.

A useful contribution to the art would be the provision of new process technology for producing racemic bridged hafnocenes, in higher yields and with better product quality at lower cost. This invention is deemed to constitute such a contribution.

SUMMARY OF THE INVENTION

It has been found that it is possible to produce hafnocenes in high yields and purity by reaction between a hafnium halide and a metallated bis(cyclopentadienyl-moiety containing) ligand, provided the hafnium halide is in the form of an adduct with a polyether, and provided further that such adduct has been formed or previously heated at a suitable elevated temperature.

In simple terms, the invention provides a process for producing a racemic, bridged hafnocene in enhanced yield, which process comprises reacting a hafnium halide-aliphatic polyether adduct that has been formed and/or previously heated at one or more temperatures of at least about 40° C., and a metallated bis(cyclopentadienyl-moiety-containing) ligand, such that a racemic, bridged hafnocene is produced. The reaction is conducted in a reaction medium that is free or at least substantially free of tetrahydrofuran and/or any other ether solvent or diluent that causes the formation of a tarry residue in the reaction mixture.

FURTHER DESCRIPTION

In accordance with one embodiment of this invention, racemic, bridged, hafnocenes are produced by a process which comprises:

a) forming a reaction mixture from
   I) at least one hafnium halide-aliphatic polyether adduct that has been formed and/or heated at one or more temperatures of at least about 40° C., and preferably at least about 60° C., said adduct as used in forming the reaction mixture being in the form of solid particles and/or in the form of a solution and/or suspension or slurry in a substantially anhydrous organic liquid solvent or diluent therefor where the adduct is present therein in whatever chemical form or forms such ligand exists when in such solution and/or suspension or slurry; and
   ii) a metallated bis(cyclopentadienyl-moiety-containing) ligand in the form of solid particles and/or in the form of a solution and/or suspension or slurry in a substantially anhydrous organic liquid solvent or diluent therefor where the ligand is present therein in whatever chemical form or forms such ligand exists when in such solution and/or suspension or slurry; and b) maintaining the temperature of the mixture at, and/or adjusting the temperature of the mixture to, one or more temperatures for a sufficient period of time such that a racemic, bridged hafnocene is produced; said mixture being free or substantially free of tetrahydrofuran and/or any other ether solvent or diluent that causes the formation of a tarry residue in the reaction mixture.

In accordance with another embodiment of this invention, racemic, bridged, hafnocenes are produced by a process which comprises:

a) forming a metal halide-polyether adduct by heating a mixture comprising at least one hafnium halide and at least one aliphatic polyether at one or more temperatures of at least about 40° C., and preferably at least about 60° C.;

b) forming a mixture from said adduct and a metallated bis(cyclopentadienyl-moiety-containing) ligand in the form of solid particles or in the form of a solution or suspension or slurry in a substantially anhydrous organic liquid solvent or diluent therefor where the ligand is present therein in whatever chemical form or forms such ligand exists when in such solution or suspension or slurry; and maintaining the temperature of the mixture at, and/or adjusting the temperature of the mixture to, one or more temperatures for a sufficient period of time such that a racemic, bridged hafnocene is produced; said mixture being free or substantially free of tetrahydrofuran and/or any other ether solvent or diluent that causes the formation of a tarry residue in the reaction mixture.

Preferably step a) of this embodiment is conducted in a liquid phase comprising at least one substantially anhydrous organic liquid solvent or diluent. Where the polyether itself is a liquid an excess quantity of the polyether can serve as the liquid phase. Alternatively, an ancillary substantially anhydrous organic liquid solvent or diluent can be employed in step a) along with the polyether, whether liquid or solid. Likewise, an ancillary substantially anhydrous organic liquid solvent or diluent can be employed in step b) of this embodiment whenever deemed necessary or desirable for providing a reaction mixture that is fluid enough to ensure good contact between the reactants and to enable efficient stirring.

For ease of reference the metallated bis(cyclopentadienyl-moiety-containing) ligand is sometimes hereinafter referred to simply as the ligand. Likewise, the hafnium halide-aliphatic polyether adduct is sometimes hereinafter referred to simply as the adduct. Before reaction with the ligand, the adduct is always heated to at least about 40° C. either during its formation or after it has been formed.

As those skilled in the art can readily understand and appreciate, the above operations should be conducted in a substantially anhydrous environment and under an inert atmosphere such as dry nitrogen, or other dry inert gases such as argon, neon, krypton, etc.

The above and other features and embodiments of the invention will be still further apparent from the ensuing description and appended claims.

Chiral hafnocenes, such as are produced in accordance with this invention are mixtures of racemic diasteriomers which have no plane of symmetry. The meso isomers, the formation of which is suppressed by this invention, have a plane of symmetry running through the hafnium atom between the rings, and thus are achiral compounds. A few examples of racemic hafnocenes producible pursuant to this invention include:

[1,1'-dimethylsilanylenebis(methylcyclopentadienyl)] hafnium dichloride;
[1,1'-dimethylsilanylenebis(indenyl)]hafnium dichloride;
[1,1'-dimethylsilanylenebis(4,5,6,7-tetrahydroindenyl)] hafnium dichloride;
[1,1'-(1,1,2,2-tetramethyldisilanylene)bis (methylcyclopentadienyl)]hafnium dichloride;
[1,1'-(1,1,2,2-tetramethyldisilanylene)bis(4,5,6,7-tetrahydroindenyl)]hafnium dichloride;
[1,1'-dimethylsilanylenebis (trimethylsilanylcyclopentadienyl)]hafnium dichloride;
[1,1'-(1,1,2,2-tetramethyldisilanylene)bis (trimethylsilanylcyclopentadienyl)]hafnium dichloride;
[1,1'-(1,1,3,3-tetramethyldisilanylene)bis(4,5,6,7-tetrahydroindenyl)]hafnium dichloride;
[1,1'-(1,1,4,4-tetramethyl-1,4-disilanylbutylene)bis(4,5,6,7-tetrahydroindenyl)]hafnium dichloride;
[1,1'-(2,2-dimethyl-2-silapropylene)bis (methylcyclopentadienyl)]hafnium dichloride;
[1,2-ethylenebis(ethylcyclopentadienyl)]hafnium dichloride;
[1,2-ethylenebis(indenyl)]hafnium dichloride;
[1,1'-dimethylsilanylenebis(methylcyclopentadienyl)] hafnium dibromide;
[1,1'-dimethylsilanylenebis(indenyl)]hafnium dibromide;
[1,1'-dimethylsilanylenebis(4,5,6,7-tetrahydroindenyl)] hafnium dibromide;
[1,1'-(1,1,2,2-tetramethyldisilanylene)bis (methylcyclopentadienyl)]hafnium dibromide;
[1,1'-(1,1,2,2-tetramethyldisilanylene)bis(4,5,6,7-tetrahydroindenyl)]hafnium dibromide;
[1,1'-dimethylsilanylenebis(methylcyclopentadienyl)] hafnium diiodide; and
[1,1'-dimethylsilanylenebis(indenyl)]hafnium diiodide.

The ligand used in the process of this invention, when in isolated and pure form, is preferably a compound of the formula

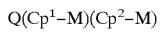

$$Q(Cp^1-M)(Cp^2-M)$$

in which $Cp^1$ and $Cp^2$ independently are cyclopentadienyl-moiety-containing groups having a ring substituent, M, where M is an alkali metal atom or a monohalomagnesium group, or where the two M's taken together are a magnesium atom; and in which Q represents a bridging group that links the Cp groups. The cyclopentadienyl-moiety-containing group before metallation is a cyclopentadienyl, indenyl, fluorenyl, or related group that can π-bond to a hafnium atom, or a hydrocarbyl (e.g., alkyl, cycloalkyl, aryl, aralkyl, alkenyl, etc.), silanyl, or hydrocarbylmetalloid substituted derivative thereof. Either or both Cp groups can have one or more hydrocarbyl ring system fused thereon. Each Cp may contain up to about 75 nonhydrogen atoms. Q may be any bridging group that is used to link the Cp groups, including, for example, silanylene ($-SiR_2-$), silaalkylene, oxasilanylene, oxasilaalkylene, benzo ($C_6H_4$ <) or substituted benzo, methylene ($-CH_2-$) or substituted methylene, ethylene ($-CH_2CH_2-$), or substituted ethylene bridges. Methylene and ethylene bridges are preferred, and ligands having silanylene bridges such as dimethylsilanylene, diethylsilanylene, ethylmethylsilanylene, dipropylsilanylene, and dibutylsilanylene are more preferred.

In forming the ligand, metallation is accomplished in known manner by deprotonating the unmetallated bridged bis(cyclopentadienyl-moiety-containing) compound with a suitable metallating agent such as an alkali metal, an alkali metal hydride, a Grignard reagent, or a dihydrocarbyl magnesium compound. Examples of deprotonating agents include sodium dispersions, lithium hydride, sodium hydride, potassium hydride, Grignard reagents, dialkylmagnesium compounds, and organoalkali metal compounds, RM, where R is a $C_1$, to $C_{10}$ hydrocarbyl group (alkyl, aryl, cycloalkyl, etc.) and M is an alkali metal. Preferred are lithium alkyls such as methyllithium, ethyllithium and butyllithium. Metallation is typically accomplished in a suitable anhydrous inert reaction medium such as a dry liquid hydrocarbon.

The adduct is formed from a hafnium tetrahalide in which the halogen atoms have an atomic number of 17 or above (i.e., atoms of chlorine, bromine and/or iodine) and a polyether capable of chelating or complexing therewith to form the adduct. Examples of such polyethers include 1,2-dimethoxyethane, 1,2-diethoxyethane, 1,2-dibutoxyethane, 1-ethoxy-2-methoxy-ethane, bis(2-methoxyethyl)ether, and the like. Most preferred are the adducts formed from hafnium tetrachloride, and especially the adducts of hafnium tetrachloride with a 1,2-dialkoxyethane in which each alkoxy group contains 1 to 4 carbon atoms. The most preferred adduct is the hafnium tetrachloride-1,2-dimethoxyethane adduct.

The ligand and the adduct can be charged to the reactor in the form of solid particles or in the form of solutions or suspensions or slurries in a substantially anhydrous organic liquid solvent or diluent therefor. When charged in neat particulate form, a separate charge of anhydrous liquid organic solvent or diluent is used so that the reaction mixture has a continuous liquid phase in which some of the reactant (s) may dissolve and in which undissolved particles of one or both reactants are suspended or slurried. Suitable solvents or diluents include inert liquid hydrocarbons, inert liquid silicones, liquid dialkylmonoethers, liquid polyethers, and mixtures thereof.

As chemists well know, when the chelate or adduct is in solution or in suspension or slurry it may, in whole or in part, change in chemical form, such as by being solvated, complexed, disassociated or otherwise transformed so that at that time it may not be completely identical in chemical structure to the way it was just prior to being placed in the form of a solution, suspension and/or slurry. If any such changes occur when forming such solutions, suspensions and/or slurries, they are within the ambit of this invention as long as ordinary skill of a chemist and common sense were used in selecting the liquid medium in which to form the solution, suspension and/or slurry.

The molar ratio of the polyether-hafnium tetrahalide adduct to the bridged ligand charged to the reactor is typically in the range of about 0.7 to about 1.3 moles (preferably 0.8 to about 1.2, more preferably about 0.9 to about 1.1 moles) of adduct per mole of ligand. A particularly preferred molar ratio is in the range of about 0.95 to about 1.05 moles of adduct per mole of ligand, as this is the most cost-effective range and simplifies work-up and purification procedures when isolating pure racemic product for use as a catalyst ingredient.

As noted above, the adduct and the ligand are fed to the reactor either as solids or as solutions or slurries. Preferably at least the ligand is charged as a solution or slurry in a suitable liquid medium, most preferably in one or more liquid aromatic hydrocarbons, or in a mixture of one or more liquid aromatic hydrocarbons with one or more liquid acyclic ethers, or in one or more liquid acyclic ethers. It is most preferred to keep the reaction mixture free of tetrahydrofuran except for trace amounts that may be carried over by one or both of the reactants. It is not known whether other cyclic ethers such as alkyltetrahydrofurans, 1,4-dioxane, tetrahydropyran, etc. will cause problems similar to those experienced when tetrahydrofuran is used with hafnium tetrahalide-polyether systems. Thus a few pilot experiments should be conducted if such other cyclic ether is selected for use to ensure that at the concentrations, temperatures and reaction times contemplated the cyclic ether will not unduly interfere with the desired reaction or unduly complicate the recovery operations such as filtration.

When reacting a hafnium halide-aliphatic polyether adduct that was formed or otherwise preheated at one or more temperatures of at least about 40° C. with the metallated ligand, a substantial portion of the reaction period can be performed at one or more temperatures in the range of about 20 to about 70° C., preferably at one or more temperatures in the range of about 20 to about 50° C., and most preferably at one or more temperatures in the range of about 25 to about 40° C., as this last named range tends to produce the highest yields of the chiral hafnocene.

Without wishing to be bound by theory, it is believed that exposure of the hafnium halide-aliphatic polyether adduct to a temperature of at least about 40° C. either during formation of the adduct or after it has been formed but before contact with the ligand may cause some presently unknown beneficial change in the adduct. For example, a $HfCl_4$-1,2-dimethoxyethane adduct made at ambient room temperature and not exposed to higher temperatures gave a poor reaction with dilithium 1,1'-dimethylsilanylene-bis(indene)-diethyletherate, whereas a $HfCl_4$-1,2-dimethoxyethane adduct made at about 80° C. gave a yield of about 70% of isolated crude racemic [1,1'-dimethylsilanylene-bis(indenyl)]hafnium dichloride under approximately the same reaction conditions. It appears therefore that the preheating of the adduct enables the achievement of higher yields of the racemic hafnocene along with enhanced reproducibility of results.

There is no universal maximum temperature above which the hafnium halide-aliphatic polyether adduct should not be heated, as this temperature will vary depending, for example, upon the composition of the adduct. However if it is desired to determine whether a given maximum temperature is suitable for use in the practice of this invention, a few pilot experiments can be conducted in the laboratory wherein the particular hafnium halide-aliphatic polyether adduct under study is heated to the given maximum temperature in a suitably high boiling aromatic hydrocarbon, and then reacted with dilithium 1,1'-dimethylsilanylene-bis-(indene)-diethyletherate using the operational procedure of Example 1 hereinafter. If the yield of racemic [1,1'-dimethylsilanylene-bis(indenyl)]hafnium dichloride is at least 40% of based on the dilithium 1,1'-dimethylsilanylene-bis(indene)-diethyletherate used, the temperature range used during such heating is suitable.

In the case of hafnium tetrachloride-polyether adducts, such as the hafnium tetrachloride-1,2-dimethoxyethane adduct, exposure to heating at one or more temperatures in the range of about 60° C. to about 110° C. during formation of the adduct or prior to its reaction with the ligand is a preferred mode of operation.

Large amounts of liquid paraffins in the reaction mixture during reaction can contribute to tar formation and reduction in yields of chiral hafnocenes. Thus the presence of such materials in the reaction mixture in which a hafnocene is being produced should be kept to a minimum, e.g., the paraffin hydrocarbon content, if any, should be kept below about 5% of the total weight of solvent/diluent.

The following Examples are provided for purposes of illustration and are not intended to limit, and should not be construed as limiting, the scope of the invention.

EXAMPLE 1

Hafnium tetrachloride (4.80 g) was slurried in toluene (32 g) for 5 minutes. 1,2-Dimethoxyethane (DME; 1.5 g) was added (while the temperature increased from 22° C. to 32° C.). The slurry was heated up, stirred at 71–78° C. for 1.5 hours and then cooled down to 30° C. A solution of dilithium 1,1'-dimethylsilanylene-bis(indene)-diethyl-etherate (formed by deprotonating 1,1'-dimethylsilanylene-bis(indene) with butyllithium in diether) (5.78 g solid; normalized NMR: 97 wt %) in DME (14.7 g) was added in a period of about 10 minutes. Toluene (5 g) was added. The reaction mass was stirred at 35° C. overnight. After filtration, and washing with toluene (5 g) and then diethylether (4 g), followed by drying, a crude product (7.28 g) was recovered. This crude product contained 74 wt % racemic [1,1'-dimethyl-silanylene-bis(indenyl)]hafnium dichloride with a trace of its meso isomer. The yield was about 67% of racemic [1,1'-dimethylsilanylene-bis(indenyl)]hafnium dichloride based on the dilithium 1,1'-dimethylsilanylene-bis(indene)-diethyletherate used. The crude product contained LiCl byproduct as the main impurity. The crude product (including the LiCl) can be subjected to methylation with methyllithium or methyl Grignard reagent to form racemic [1,1'-dimethylsilanylene-bis(indenyl)]hafnium dimethyl.

EXAMPLE 2

A slurry of hafnium tetrachloride (6.40 g) in toluene (40 g) was stirred in a 100 mL flask for 5 minutes. DME (2.0 g)

was added to the slurry (while the temperature increased from 23 to 35° C.). The mixture was heated up to and held at 70–82° C. for 1.6 hours and then cooled down. A solution of dilithium 1,1'-dimethylsilanylene-bis(indene)-diethyletherate formed using the same type of procedure as in Example 1 (7.87 g of 97 wt % normalized purity)) in DME (19.4 g) was added in about 5 minutes (while the temperature rose from 28 to 30° C.). The reaction mass was stirred at 30–36° C. for 2.3 hours and then heated up and held at 65–70° C. for 0.5 hour. After this mixture cooled down, the reaction slurry was filtered. The wet cake was washed with toluene (7 g), treated with $Et_2O$ (5 g for 1 hour) and thereafter washed with 2 g of $Et_2O$ and dried to obtain crude product (9.91 g) containing 77 wt % of racemic [1,1'-dimethylsilanylene-bis(indenyl)]hafnium dichloride with a trace of meso isomer and DME. The yield was about 71% based on HfCl4 (or 70% based on the dilithium 1,1'-dimethylsilanylene-bis(indene)-diethyletherate).

The yields of hafnocenes formed using prior published process technologies have, in general, been relatively low (e.g., in the range of about 25–30%), and filtration of the hafnocene product has often proved to be difficult. Repeated attempts to improve the hafnocene yields and filterability by process modifications often met with failure, either with no improvements or in some cases with further loss in yields and even poorer filterability characteristics. Also the reaction mass tended to comprise mixtures of racemic and meso diastereomers along with other unidentifiable by-products and tars. Thus by virtue of the results achievable by the practice of this invention as illustrated by Examples 1 and 2, this invention as applied to synthesis of bridged hafnocenes, is deemed to constitute an especially important contribution to the art.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, salvation, ionization, or other transformation during the course of contacting, blending or mixing operations, if done in accordance with the disclosure hereof and with the use of ordinary skill of a chemist and common sense, is within the purview and scope of this invention.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
    a) forming a reaction mixture from
        i) at least one hafnium halide-aliphatic polyether adduct that has been formed and/or heated at one or more temperatures of at least about 40° C., said adduct as used in forming the reaction mixture being in the form of solid particles and/or in the form of a solution and/or suspension or slurry in a substantially anhydrous organic liquid solvent or diluent therefor where the adduct is present therein in whatever chemical form or forms such ligand exists when in such solution and/or suspension or slurry; and
        ii) a metallated bis(cyclopentadienyl-moiety-containing) ligand in the form of solid particles and/or in the form of a solution and/or suspension or slurry in a substantially anhydrous organic liquid solvent or diluent therefor where the ligand is present therein in whatever chemical form or forms such ligand exists when in such solution and/or suspension or slurry; and
    b) maintaining the temperature of the mixture at, and/or adjusting the temperature of the mixture to, one or more temperatures for a sufficient period of time such that a racemic, bridged hafnocene is produced; said mixture being substantially free of tetrahydrofuran and/or any other ether solvent or diluent that causes the formation of a tarry residue in the reaction mixture.

2. A process according to claim 1 wherein said hafnium halide-aliphatic polyether adduct in i) has been formed and/or heated at one or more temperatures of at least about 60° C.

3. A process according to claim 1 wherein said hafnium halide-aliphatic polyether adduct in i) is a hafnium tetrahalide adduct.

4. A process according to claim 1 wherein said hafnium halide-aliphatic polyether adduct in i) is a hafnium tetrachloride adduct.

5. A process according to claim 1 wherein said hafnium halide-aliphatic polyether adduct in i) is a hafnium tetrachloride-1,2-dimethoxyethane adduct.

6. A process according to claim 5 wherein said hafnium tetrachloride-1,2-dimethoxy-ethane adduct has been formed and/or heated at one or more temperatures in the range of about 60° C. to about 110° C.

7. A process according to claim 1 wherein said adduct in i) is a hafnium tetrachloride-1,2-dimethoxyethane adduct, and wherein said ligand in ii) is dilithium 1,1'-dimethylsilanylene-bis(indene).

8. A process according to claim 2 wherein said adduct in i) is a hafnium tetrachloride-1,2-dimethoxyethane adduct, and wherein said ligand in ii) is dilithium 1,1'-dimethylsilanylene-bis(indene).

9. A process which comprises:
    a) forming a metal halide-polyether adduct by heating a mixture comprising at least one hafnium halide and at least one aliphatic polyether at one or more temperatures of at least about 40° C., said mixture being substantially free of tetrahydrofuran and/or any other ether solvent or diluent that causes the formation of a tarry residue in the reaction mixture;
    b) forming a mixture from said adduct and a metallated bis(cyclopentadienyl-moiety-containing) ligand in the form of solid particles or in the form of a solution or suspension or slurry in a substantially anhydrous organic liquid solvent or diluent therefor where the ligand is present therein in whatever chemical form or forms such ligand exists when in such solution or suspension or slurry; and maintaining the temperature of the mixture at, and/or adjusting the temperature of the mixture to, one or more temperatures for a sufficient period of time such that a racemic, bridged hafnocene is produced; said mixture of b) being substantially free of tetrahydrofuran and/or any other ether solvent or diluent that causes the formation of a tarry residue in the reaction mixture.

10. A process according to claim 9 wherein a) is performed at one or more temperatures of at least about 60° C.

11. A process according to claim 9 wherein said hafnium halide in a) is a hafnium tetrahalide.

12. A process according to claim 11 wherein a) is performed at one or more temperatures of at least about 60° C.

13. A process according to claim 9 wherein said hafnium halide in a) is hafnium tetrachloride.

14. A process according to claim 13 wherein a) is performed at one or more temperatures of at least about 60° C.

15. A process according to claim 9 wherein in a) said hafnium halide is hafnium tetrachloride and said polyether is 1,2-dimethoxyethane.

16. A process according to claim 15 wherein a) is performed at one or more temperatures in the range of about 60° C. to about 110° C.

17. A process according to claim 9 wherein the polyether in b) is 1,2-dimethoxyethane.

18. A process according to claim 9 wherein the adduct in a) is a hafnium tetrachloride-1,2-dimethoxyethane adduct, and wherein the ligand in b) is dilithium 1,1'-dimethylsilanylene-bis(indene).

19. A process for producing a racemic, bridged hafnocene in enhanced yield, which process comprises reacting a hafnium halide-aliphatic polyether adduct that has been formed and/or previously heated at one or more temperatures of at least about 40° C., and a metallated bis(cyclopentadienyl-moiety-containing) ligand, such that a racemic, bridged hafnocene is produced, said process being conducted in a reaction medium that is substantially free of tetrahydrofuran and/or any other ether solvent or diluent that causes the formation of a tarry residue in the reaction mixture.

20. A process according to claim 19 wherein the reaction is performed in a substantially anhydrous organic liquid solvent or diluent.

21. A process according to claim 20 wherein the hafnium halide is a hafnium tetrahalide.

* * * * *